United States Patent
Zile et al.

(10) Patent No.: US 12,220,212 B2
(45) Date of Patent: Feb. 11, 2025

(54) PHENOTYPING SENSOR PATTERNS TO IDENTIFY AND TREAT HEART FAILURE

(71) Applicant: Cardiac Pacemakers, Inc., St. Paul, MN (US)

(72) Inventors: Melanie Anne Zile, Baltimore, MD (US); Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 798 days.

(21) Appl. No.: 15/830,893

(22) Filed: Dec. 4, 2017

(65) Prior Publication Data
US 2018/0153416 A1 Jun. 7, 2018

Related U.S. Application Data

(60) Provisional application No. 62/431,050, filed on Dec. 7, 2016.

(51) Int. Cl.
| | |
|---|---|
| *A61B 5/0205* | (2006.01) |
| *A61B 5/00* | (2006.01) |
| *A61N 1/362* | (2006.01) |
| *A61N 1/365* | (2006.01) |
| *A61N 1/372* | (2006.01) |
| *A61N 1/39* | (2006.01) |
| *A61B 5/024* | (2006.01) |
| *A61B 5/0531* | (2021.01) |
| *A61B 5/08* | (2006.01) |

(Continued)

(52) U.S. Cl.
CPC ........ *A61B 5/02055* (2013.01); *A61B 5/7246* (2013.01); *A61B 5/7264* (2013.01); *A61N 1/3627* (2013.01); *A61N 1/36585* (2013.01); *A61N 1/37252* (2013.01); *A61N 1/3956* (2013.01); *A61N 1/39622* (2017.08); *A61B 5/024* (2013.01); *A61B 5/0531* (2013.01); *A61B 5/0816* (2013.01); *A61B 5/1118* (2013.01); *A61B 7/04* (2013.01)

(58) Field of Classification Search
CPC ..... A61B 5/02055; A61B 5/024; A61B 5/046; A61B 5/7275; A61B 8/5223
See application file for complete search history.

(56) References Cited

U.S. PATENT DOCUMENTS

| | | | |
|---|---|---|---|
| 2006/0282000 A1* | 12/2006 | Zhang ................. | A61N 1/3627 600/528 |
| 2012/0157856 A1* | 6/2012 | An ........................ | G16H 40/67 600/484 |

OTHER PUBLICATIONS

Shah et al. "Phenomapping of Novel Classification of Heart Failure With Preserved Ejection Fraction", vol. 131, No. 3, Nov. 14, 2014, pp. 269-279 (Year: 2014).*

(Continued)

*Primary Examiner* — Tse W Chen
*Assistant Examiner* — Michael A Catina
(74) *Attorney, Agent, or Firm* — Schwegman Lundberg & Woessner, P.A.

(57) ABSTRACT

This document discusses, among other things, systems and methods to receive physiologic information from a patient and to generate a heart failure status using the received physiologic information. Based on the received physiologic information, the generated heart failure status can be classified into at least one of a set of predetermined phenotype clusters.

20 Claims, 5 Drawing Sheets

(51) Int. Cl.
*A61B 5/11* (2006.01)
*A61B 7/04* (2006.01)

(56) References Cited

OTHER PUBLICATIONS

Choi, Edward, et al., "Medical Concept Representation Learning from Electronic Health Records and its Application on Heart Failure Prediction", Georgia Institute of Technology, Atlanta, USA, Research Development & Dissemination, Sutter Health, Walnut Creek, USA, 45 pages, Feb. 2016.
Panahiazar, Maryam, et al., "Using EHRs and Machine Learning for Heart Failure Survival Analysis", https://www.ncbi.nlm.nih.gov/pmc/articles/PMC4905764, 7 pages Dec. 4, 2017.
"International Application Serial No. PCT/US2017/064521, International Preliminary Report on Patentability mailed Jun. 20, 2019", 8 pgs.
"International Application Serial No. PCT/US2017/064521, International Search Report mailed Mar. 21, 2018", 4 pgs.
"International Application Serial No. PCT/US2017/064521, Written Opinion mailed Mar. 21, 2018", 6 pgs.
Katz, Daniel H, et al., "Phenomapping for the Identification of Hypertensive Patients with the Myocardial Substrate for Heart Failure with Preserved Ejection Fraction", Journal of Cardiovascular Translational Research Springer US Boston, vol. 10 No. 3, (Mar. 3, 2018), 275-284.

\* cited by examiner

PHENOTYPING SENSOR PATTERNS TO IDENTIFY AND TREAT HEART FAILURE

CLAIM OF PRIORITY

This application claims the benefit of priority under 35 U.S.C. § 119(e) of U.S. Provisional Patent Application Ser. No. 62/431,050, filed on Dec. 7, 2016, which is herein incorporated by reference in its entirety.

TECHNICAL FIELD

This document relates generally to medical devices, and more particularly, but not by way of limitation, to systems, devices, and methods to treat heart failure in a patient.

BACKGROUND

Heart failure refers to a clinical syndrome in which cardiac function causes a below normal cardiac output that can fall below a level adequate to meet the metabolic demand of peripheral tissues. Heart failure may present itself as congestive heart failure due to the accompanying venous and pulmonary congestion. Heart failure can be due to a variety of etiologies, such as ischemic heart disease. Cardiac decompensation is typically marked by dyspnea (difficulty breathing), venous engorgement and edema, and each decompensation event can cause further long term deterioration of the heart function.

SUMMARY

This document discusses, among other things, systems and methods to monitor physiologic parameters in a patient and to generate a heart failure status using the received physiologic information. The heart failure status can be classified into a predetermined phenotype cluster based on the received physiologic information. The predetermined phenotype clusters can be determined based on a plurality of heart failure statuses collected from a group of patients. Patient data can be correlated with the predetermined phenotype clusters. A medical treatment can be determined based on the at least one predetermined phenotype cluster that the generated heart failure status can be classified into.

An example (e.g., "Example 1") of subject matter (e.g., a system) may include a signal analysis circuit configured to receive physiologic information from a patient, and to generate a heart failure status using the received physiologic information. The system may also include a control circuit configured to classify the generated heart failure status into at least one of a set of predetermined phenotype clusters based on the received physiologic information.

In Example 2, the subject matter of Example 1 may optionally be configured such that the set of predetermined phenotype clusters are determined based on a plurality of heart failure statuses collected from a group of patients.

In Example 3, the subject matter of any one or more of Examples 1-2 may optionally be configured such that the set of predetermined phenotype clusters are correlated with patient data collected from the group of patients based on a statistical relationship between the set of predetermined clusters and the patient data.

In Example 4, the subject matter of Example 3 may optionally be configured such that the control circuit is further configured to determine a medical treatment for the patient based on the patient data from the group of patients correlated with the set of predetermined phenotype clusters.

In Example 5, the subject matter of any one or more of Examples 3-4 may optionally be configured such that the patient data includes at least one of a patient medication, a patient heart condition, a patient disease, or a medical history of the patient.

In Example 6, the subject matter of any one or more of Examples 1-5 may optionally be configured such that the control circuit is further configured to determine a medical treatment for the patient based on the at least one predetermined phenotype cluster that the generated heart failure status is classified into.

In Example 7, the subject matter of any one or more of Examples 1-6 may optionally be configured such that the at least one of the set of predetermined phenotype clusters includes a portion of physiologic information statistically correlated with physiologic information associated with the generated heart failure status.

In Example 8, the subject matter of any one or more of Examples 1-7 may optionally be configured such that the received physiologic information from the patient includes at least one of a heart sound signal, an impedance signal, a respiratory signal, an activity signal, a pressure signal, a biomarker signal, a pulse plethysmographic signal, a temperature signal, or a heart rate signal.

An example (e.g., "Example 9") of subject matter (e.g., a method) may include receiving physiologic information from a patient. The method may also include generating a heart failure status using the received physiologic information. The method may also include classifying the generated heart failure status into at least one of a set of predetermined phenotype clusters based on the received physiologic information.

In Example 10, the subject matter of Example 9 may optionally include determining the set of predetermined phenotype clusters based on a plurality of heart failure statuses collected from a group of patients.

In Example 11, the subject matter of any one or more of Examples 9-10 may optionally include correlating the set of predetermined phenotype clusters with patient data collected from the group of patients based on a statistical relationship between the set of predetermined clusters and the patient data.

In Example 12, the subject matter of Example 11 may optionally include determining a medical treatment for the patient based on the patient data from the group of patients correlated with the set of predetermined phenotype clusters.

In Example 13, the subject matter of any one or more of Examples 11-12 may optionally be configured such that the patient data includes at least one of a patient medication, a patient heart condition, a patient disease, or a medical history of the patient.

In Example 14, the subject matter of any one or more of Examples 9-13 may optionally include determining a medical treatment for the patient based on the at least one predetermined phenotype cluster that the generated heart failure status is classified into.

In Example 15, the subject matter of any one or more of Examples 9-14 may optionally be configured such that the at least one of the set of predetermined phenotype clusters includes a portion of physiologic information statistically correlated with physiologic information associated with the generated heart failure status.

An example (e.g., "Example 16") of subject matter (e.g., a system) may include a signal analysis circuit configured to receive physiologic information from a patient and to generate a heart failure status using the received physiologic information. The system may also include a control circuit configured to classify the generated heart failure status into at least one of a set of predetermined phenotype clusters based on the received physiologic information.

In Example 17, the subject matter of Example 16 may optionally be configured such that the set of predetermined phenotype clusters are determined based on a plurality of heart failure statuses collected from a group of patients.

In Example 18, the subject matter of Example 17 may optionally be configured such that the set of predetermined phenotype clusters are correlated with patient data collected from the group of patients based on a statistical relationship between the set of predetermined clusters and the patient data.

In Example 19, the subject matter of Example 18 may optionally be configured such that the control circuit is further configured to determine a medical treatment for the patient based on the patient data from the group of patients correlated with the set of predetermined phenotype clusters.

In Example 20, the subject matter of Example 19 may optionally be configured such that the patient data includes at least one of a patient medication, a patient heart condition, a patient disease, or a medical history of the patient.

In Example 21, the subject matter of Example 16 may optionally be configured such that the control circuit is further configured to determine a medical treatment for the patient based on the at least one predetermined phenotype cluster that the generated heart failure status is classified into.

In Example 22, the subject matter of Example 16 may optionally be configured such that the at least one of the set of predetermined phenotype clusters includes a portion of physiologic information statistically correlated with physiologic information associated with the generated heart failure status.

In Example 23, the subject matter of Example 16 may optionally be configured such that the received physiologic information from the patient includes at least one of a heart sound signal, an impedance signal, a respiratory signal, an activity signal, a pressure signal, a biomarker signal, a pulse plethysmographic signal, a temperature signal or a heart rate signal.

An example (e.g., "Example 24") of subject matter (e.g., a method) may include receiving physiologic information from a patient. The method may also include generating a heart failure status using the received physiologic information. The method may also include classifying the generated heart failure status into at least one of a set of predetermined phenotype clusters based on the received physiologic information.

In Example 25, the subject matter of Example 24 may optionally include determining the set of predetermined phenotype clusters based on a plurality of heart failure statuses collected from a group of patients.

In Example 26, the subject matter of Example 25 may optionally include correlating the set of predetermined phenotype clusters with patient data collected from the group of patients based on a statistical relationship between the set of predetermined clusters and the patient data.

In Example 27, the subject matter of Example 26 may optionally include determining a medical treatment for the patient based on the patient data from the group of patients correlated with the set of predetermined phenotype clusters.

In Example 28, the subject matter of Example 27 may optionally include the patient data includes at least one of a patient medication, a patient heart condition, a patient disease, or a medical history of the patient.

In Example 29, the subject matter of Example 24 may optionally include determining a medical treatment for the patient based on the at least one predetermined phenotype cluster that the generated heart failure status is classified into.

In Example 30, the subject matter of Example 24 may optionally be configured such that the at least one of the set of predetermined phenotype clusters includes a portion of physiologic information statistically correlated with physiologic information associated with the generated heart failure status.

In Example 31, the subject matter of Example 24 may optionally be configured such that the received physiologic information from the patient includes at least one of a heart sound signal, an impedance signal, a respiratory signal, an activity signal, a pressure signal, a biomarker signal, a pulse plethysmographic signal, a temperature signal or a heart rate signal.

An example (e.g., "Example 32") of subject matter (e.g., a non-transitory machine-readable medium) may include instructions that when executed by a machine, cause the machine to receive physiologic information from a patient. The non-transitory machine-readable medium may also include instructions that when executed by a machine, cause the machine to generate a heart failure status using the received physiologic information.

In Example 33, the subject matter of Example 32 may optionally include instructions, which when executed by the machine, cause the machine to determine a medical treatment for the patient based on patient data from the group of patients correlated with the set of predetermined phenotype clusters, wherein the set of predetermined phenotype clusters are correlated with patient data collected from the group of patients based on a statistical relationship between the set of predetermined phenotype clusters and the patient data.

In Example 34, the subject matter of Example 33 may optionally be configured such that the patient data includes at least one of a patient medication, a patient heart condition, a patient disease, or a medical history of the patient.

In Example 35, the subject matter of Example 33 may optionally include instructions, which when executed by the machine, cause the machine to determine a medical treatment for the patient based on the at least one predetermined phenotype cluster that the generated heart failure status is classified into.

An example (e.g., "Example 36") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Monitoring heart failure patients and detecting physiologic information indicative of a heart failure decompensation event can reduce a worsening of heart failure in heart failure patients, and can reduce costs associated with hospitalization of heart failure patients. Additionally, identification of patients at an elevated risk of a heart failure decompensation event can help ensure timely treatment, thereby improving the prognosis and patient outcome. Identifying and safely managing the patients at risk for future heart failure decompensation events can avoid unnecessary medical intervention and reduce healthcare costs.

Medical devices can be used for monitoring a patient and detecting physiologic information. Examples of such medical devices can include implantable medical devices (IMD), subcutaneous medical devices, wearable medical devices or other external medical devices. The medical devices can include physiologic sensors configured to sense one or more of electrical activity or mechanical function of the heart, or physical or physiologic variables associated with the signs and symptoms of heart failure. Some of these devices can provide diagnostic features, such as using transthoracic impedance or other sensor signals.

Various embodiments described herein can provide improved detection, prediction, or treatment of a heart failure decompensation event. The present inventors have recognized, among other things, that by providing a medical treatment based on the formation of phenotype clusters, heart failure decompensation events can be detected or predicted more accurately and treatment can be administered more efficiently. The formation and use of phenotype clusters, such as in one or more medical devices as described herein, can provide one or more of an improved speed of detection or prediction of heart failure decompensation events, a reduction in an amount of processing required to detect or predict a heart failure decompensation event, a reduction in an amount of memory required to detect or predict a heart failure decompensation event, or a reduction in power otherwise consumed by the one or more medical devices in detecting or predicting a heart failure decompensation event. In certain examples, the reduced processing, memory, and power requirements can result in a smaller, less intrusive, or less costly physical devices. In other examples, such reductions can enable a device to perform other functions without increasing cost, size, or otherwise affecting existing device performance, or can extend the usable life of a medical device configured to detect or predict a heart failure decompensation event.

Figure 1:
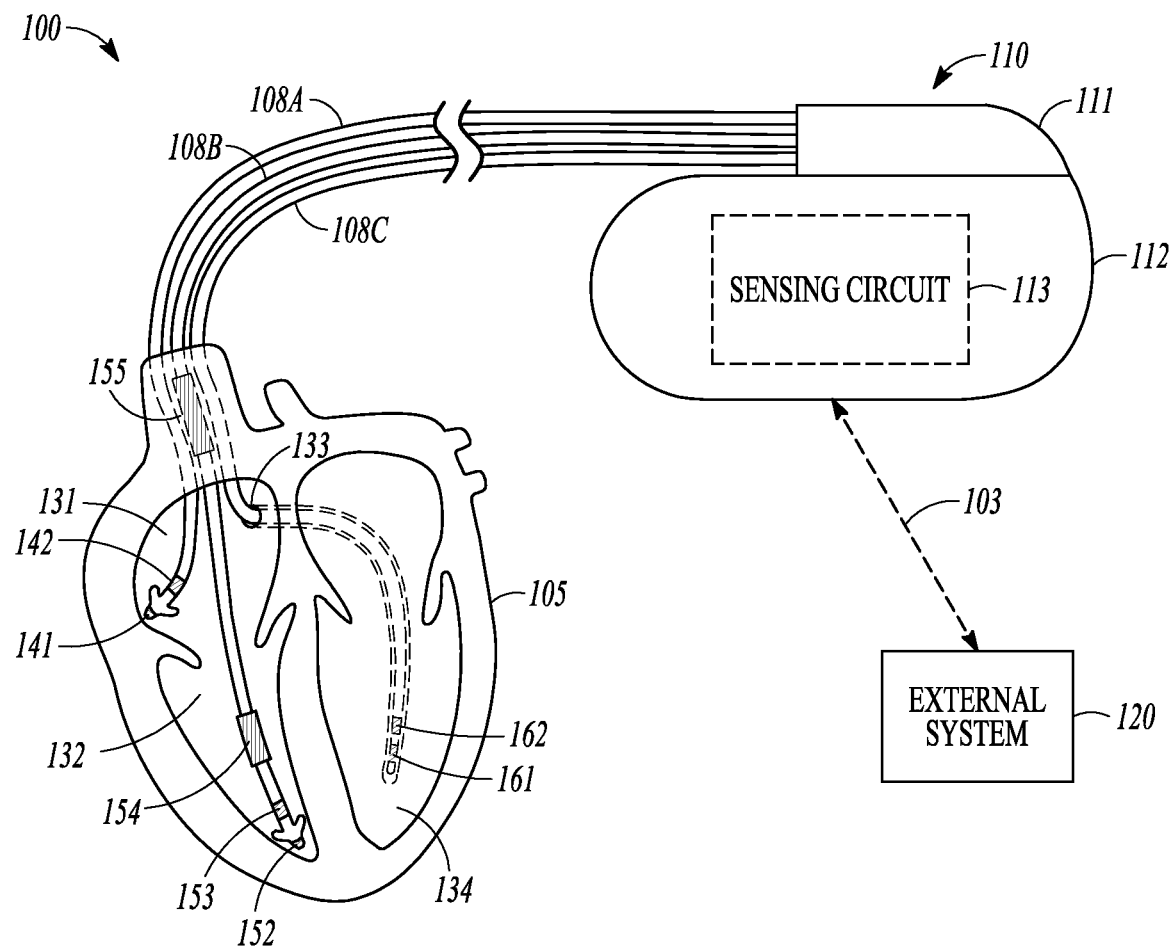
FIG. 1 illustrates an example system including a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include a medical device, such as an implantable medical device (IMD) 110 that can be electrically coupled to a heart 105, such as through one or more leads 108A-C, and an external system 120 that can communicate with the IMD 110, such as via a communication link 103. The IMD 110 can include an implantable cardiac device, such as a pacemaker, an implantable cardioverter-defibrillator (ICD), or a cardiac resynchronization therapy (CRT) device. The IMD 110 can include one or more monitoring or therapeutic devices, such as a subcutaneously implanted device, a wearable external device, a neural stimulator, a drug delivery device, a biological therapy device, or one or more other medical devices. The IMD 110 can be coupled to a monitoring medical device, such as a bedside or other external monitor.

As illustrated in FIG. 1, the IMD 110 can include a hermetically sealed can 112 that can house an electronic circuit that can sense a physiologic signal in the heart 105 and can deliver one or more therapeutic electrical stimulations to a target region, such as in the heart, such as through one or more leads 108A-C. The CRM system 100 can include only one lead, such as 108B, or can include two leads, such as 108A and 108B.

The lead 108A can include a proximal end that can be configured to be connected to IMD 110 and a distal end that can be configured to be placed at a target location, such as in the right atrium (RA) 131 of the heart 105. The lead 108A can have a first pacing/sensing electrode 141 that can be located at or near a distal end of the lead 108A, and a second pacing/sensing electrode 142 that can be located at or near the first pacing/sensing electrode 141. The first and second pacing/sensing electrodes 141 and 142 can be electrically connected to the IMD 110, such as via separate conductors in the lead 108A, such as to allow for sensing of the right atrial activity and optional delivery of atrial pacing pulses.

The lead 108B can be a defibrillation lead that can include a proximal end that can be connected to IMD 110 and a distal end that can be placed at a target location, such as in the right ventricle (RV) 132 of heart 105. The lead 108B can have a first pacing/sensing electrode 152 that can be located at distal end, a second pacing/sensing electrode 153 that can be located near the first pacing/sensing electrode 152, a first defibrillation coil electrode 154 that can be located near the second pacing/sensing electrode 153, and a second defibrillation coil electrode 155 that can be located at a distance from the distal end, such as for superior vena cava (SVC) placement. The first pacing/sensing electrode 152, the second pacing/sensing 153, the first defibrillation coil electrode 154, and the second defibrillation coil electrode 155 can be electrically connected to the IMD 110, such as via separate conductors in the lead 108B. The first pacing/sensing electrode 152 and the second pacing/sensing electrode 153 can allow for sensing of a ventricular electrogram (EGM) and can optionally allow delivery of one or more ventricular pacing pulses, and the first defibrillation coil electrode 154 and the second defibrillation coil electrode 155 can allow for delivery of one or more ventricular cardioversion/defibrillation pulses.

In an example, the lead 108B can include only the first pacing/sensing electrode 152, the first defibrillation coil electrode 154, and the second defibrillation coil electrode 155. The first pacing/sensing electrode 152 and the first defibrillation coil electrode 154 can be used for sensing or delivery of one or more ventricular pacing pulses, and the first defibrillation coil electrode 154 and the second defibrillation coil electrode 155 can be used for delivery of one or more ventricular cardioversion or defibrillation pulses.

The lead 108C can include a proximal end that can be connected to the IMD 110 and a distal end that can be configured to be placed at a target location, such as in a left ventricle (LV) 134 of the heart 105. The lead 108C can be implanted through the coronary sinus 133 and can be placed in a coronary vein over the LV, such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMB 110, such as via separate conductors in the lead 108C, such as to allow for sensing of the LV EGM and optionally allow delivery of one or more resynchronization pacing pulses from the LV.

The IMB 110 can include one or more electronic circuits configured to sense one or more physiologic signals. In an example, the physiologic signal can include an EGM or a signal representing mechanical function of the heart 105. The hermetically sealed can 112 can function as an electrode, such as for sensing or pulse delivery. For example, an electrode from one or more of the leads 108A-C can be used together with the can 112, such as for unipolar sensing of a EGM or for delivering one or more pacing pulses. A defibrillation electrode from the lead 108B can be used together with the can 112, such as for delivering one or more cardioversion/defibrillation pulses.

In an example, the IMD 110 can sense an impedance, such as an impedance between electrodes located on one or more of the leads 108A-C or the can 112. The IMB 110 can be configured to inject current between a pair of electrodes, sense the resultant voltage between the same or different pair of electrodes, and determine an impedance (e.g., using Ohm's Law). The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or a tetrapolar configuration in which the electrodes used for current injection can be distinct from the electrodes used for voltage sensing. In an example, the IMB 110 can be configured to inject current between an electrode on the RV lead 108B and the can housing 112, and to sense the resultant voltage between the same electrodes or between a different electrode on the RV lead 108B and the can housing 112.

A physiologic signal can be sensed from one or more physiologic sensors that can be integrated within the IMD 110. The IMB 110 can also be configured to sense a physiologic signal from one or more external physiologic sensors or one or more external electrodes coupled to the IMB 110. Examples of the physiologic signal can include one or more of intrathoracic impedance, intracardiac impedance, arterial pressure, pulmonary artery pressure, RV pressure, LV coronary pressure, coronary blood temperature, heart rate, blood oxygen saturation, one or more heart sounds, physical activity or exertion level, posture, respiration, body weight, or body temperature.

As illustrated, the CRM system 100 can include a sensing circuit 113. The sensing circuit 113 can be coupled to one or more physiologic sensors or sensing electrodes, such as the electrodes on one or more of the leads 108A-C, such as to receive physiologic signals from the physiologic sensors or electrodes.

The external system 120 can allow for programming of the IMB 110 and can receive information about one or more signals acquired by IMD 110, such as can be received via a communication link 103. The external system 120 can include a local external IMB programmer. The external system 120 can include a remote patient management system that can monitor patient status or adjust one or more therapies, such as from a remote location.

The communication link 103 can include one or more of an inductive telemetry link, a radio-frequency telemetry link, or a telecommunication link, such as an internet connection. The communication link 103 can provide for data transmission between the IMB 110 and the external system 120. The transmitted data can include, for example, real-time physiologic data acquired by the IMD 110, physiologic data acquired by and stored in the IMD 110, therapy history data or data indicating IMD operational status stored in the IMD 110, one or more programming instructions to the IMD 110, such as to configure the IMB 110 to perform one or more actions that can include physiologic data acquisition, such as using programmably specifiable sensing electrodes and configuration, device self-diagnostic test, or delivery of one or more therapies.

The sensing circuit 113 can be implemented at the external system 120, which can be configured to perform target event detection, such as using data extracted from the IMD 110 or data stored in a memory within the external system 120. Portions of the sensing circuit 113 can be distributed between the IMD 110 and the external system 120. In an example, the external system 120 can be implemented entirely within the IMD 100.

Portions of the IMD 110 or the external system 120 can be implemented using hardware, software, or any combination of hardware and software. Portions of the IMD 110 or the external system 120 can be implemented using an application-specific circuit that can be constructed or configured to perform one or more particular functions, or can be implemented using a general purpose circuit that can be programmed or otherwise configured to perform one or more particular functions. Such a general purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general purpose circuit that can be driven by a code instructing a portion of the general purpose circuit to perform a comparison between the two signals.

Figure 2:
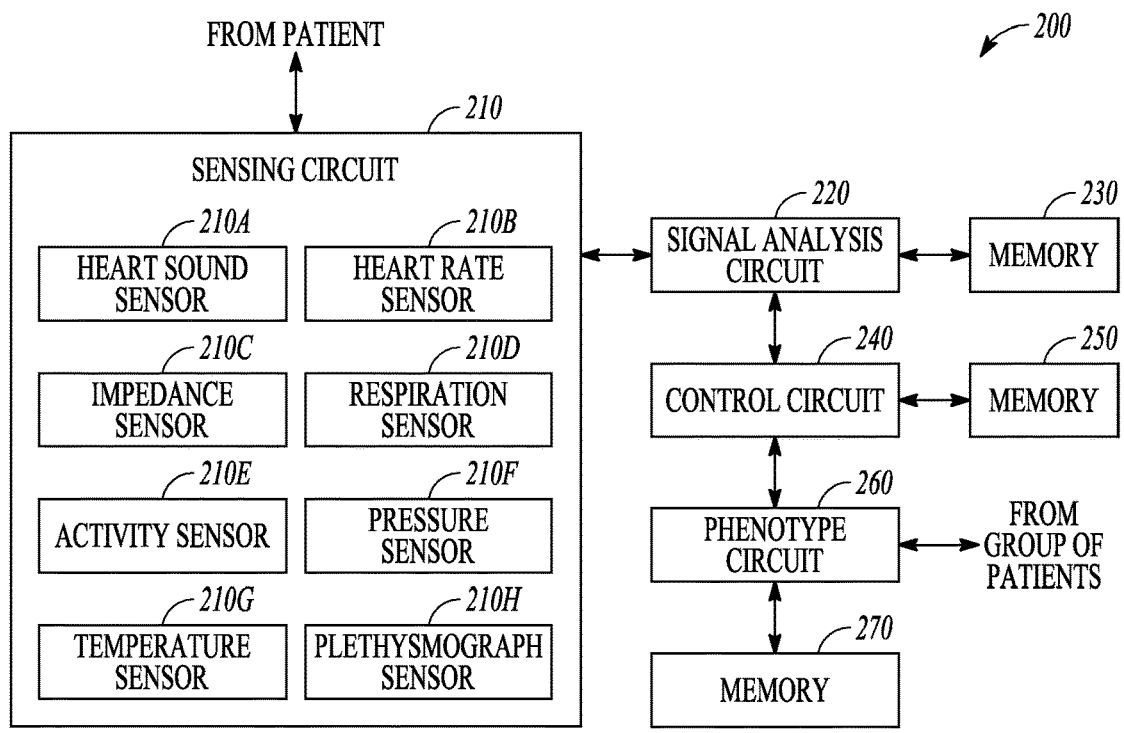
FIG. 2 illustrates an example system including a heart failure treatment system.

FIG. 2 illustrates an example heart failure treatment system 200 for detecting or determining heart failure or worsening heart failure in a patient. The heart failure treatment system 200 can include sensing circuit 210, signal analysis circuit 220, a memory 230, a control circuit 240, a memory 250, a phenotype circuit 260, and a memory 270. The sensing circuit 210 can include a heart sound sensor 210A (e.g., an accelerometer, a microphone, etc.), a heart rate sensor 210B (e.g., an electrocardiogram (ECG) sensor), an impedance sensor 210C, a respiration sensor 210D, an activity sensor 210E (e.g., an accelerometer), a pressure sensor 210F, a temperature sensor 210G, a plethysmograph sensor 210H, or one or more other sensors configured to sense physiologic information from a patient. The sensing circuit 210 can be connected to the signal analysis circuit 220. The signal analysis circuit 220 can be connected to the memory 230 and the control circuit 240. The control circuit 240 can be connected to the memory 250 and to the phenotype circuity 270. The phenotype circuit 260 can be connected to the memory 270.

In an example, the heart rate sensor 210B can be configured to sense a heart rate or heart rate information of the patient, or one or more other amplitude or timing of one or more features of the electrical information of the heart (e.g., an R-wave amplitude or timing, or one or more other amplitudes, intervals, or timings of one or more other features, etc.). In certain examples, information from the heart rate sensor can be combined with information from one or more other sensors in the sensing circuit 210.

In an example, the respiration sensor 210D can be configured to configured to sense a one or more of a respiratory rate, a tidal volume, or a minute ventilation of the patient. In certain examples, the respiration sensor 210D can be configured to determine a rapid shallow breathing index (RSBI) (e.g., the respiratory rate divided by the tidal volume), such as to provide an indication of shortness of breath of a patient.

In an example, the heart sound sensor 210A can be configured to sense one or more heart sound signals, such as a first heart sound (S1), a second heart sound (S2), a third heart sound (S3), or a fourth heart sound (S4), or one or more features, timings, or intervals between one or more heart sounds and one or more other physiologic signals. For example, the heart sound sensor 210A can be configured to sense a third heart sound (S3) that, among other things, can provide an indication of an elevated filling pressure. In an example, the heart sound sensor 210A can sense a first heart sound (S1) that, among other things, can provide an indication of contractility. In other examples, the heart sound sensor 210A can be configured to sense both S3 and S1, or can be configured to provide a normalized or other ratio of one or more of the heart sounds (e.g., S3/S1, etc.).

In an example, the impedance sensor 210C can be configured to sense an intrathoracic, a transthoracic, or other impedance information from the patient. The impedance information can be used to determine a fluid status of the patient, to assess lead integrity or electrode placement, or to detect respiration information.

In an example, a first portion of the heart failure treatment system 200 can be located in an implantable medical device, such as one or more of the sensors in the sensing circuit 210, and a second portion of the heart failure treatment system 200 can be located in an external system or an external medical device, such as a wearable medical device, etc. In other examples, the entirety of the heart failure treatment system 200 can be located in the implantable medical device 110.

During operation, the sensing circuit 210 can sense a physiologic parameter and provide at least one sensed physiologic parameter to the signal analysis circuitry 220. The signal analysis circuitry 220 can receive the at least one sensed physiologic parameter and can store the at least one sensed physiologic parameter in the memory 230.

The signal analysis circuitry 220 can create an index for each of the at least one sensed physiologic parameters. The indices can be determined based on a statistical analysis of the stored sensed physiologic parameters (e.g., a mean, a variance, a correlation, a covariance, etc.). In an example, the statistical analysis can include a range, an inter-quartile range, a standard deviation, a variance, a sample variance, or other first-order, second-order, or higher-order statistics. In an example, the indices can include a numerical value in a predetermined range (e.g., 1 to 20). An index having a value near the high or low end of the predetermined range (e.g., within 25% of the high or low end of the predetermined range, or within 50% of the high end of the predetermined range, etc.) can provide an indication that the sensed physiologic parameter corresponding to the index can have a value significantly outside a normal range (e.g., the sensed physiologic parameter can include a statistically abnormal value).

A composite index can be formed from the indices. In an example, the composite index can include N indices. The composite index can include a numerical value in a predetermined range (e.g., 0-100). The signal analysis circuitry 220 can generate a heart failure status based on the numerical value of the composite index. In an example, the signal analysis circuitry 220 can generate a heart failure status based on the numerical value of a single index. In an example, the signal analysis circuitry 220 can generate a heart failure status based on the numerical value of one or more indices. The heart failure status can indicate an increased risk of a heart failure decompensation event. The heart failure status and the sensed physiologic parameters associated with the heart failure status can be transmitted to the control circuit 240. The control circuit 240 can store the sensed physiologic parameters and the associated heart failure status in the memory 250. The control circuit 240 can then classify the received heart failure status into a predetermined phenotype cluster based on the N indices (e.g., a phenotype cluster that has been previously determined).

The predetermined phenotype cluster that the heart failure status is classified into can be one of a number of predetermined phenotype clusters (e.g., there can be five predetermined phenotype clusters and the control circuit 240 can classify the received heart failure status into one of the five predetermined phenotype clusters). The predetermined phenotype clusters can each include a collection of heart failure statuses and associated physiologic parameters collected from a group of patients. The predetermined phenotype clusters can also include patient data correlated with the collection of heart failure statuses and associated physiologic parameters. The control circuit 240 can then determine a medical treatment for patient based on the predetermined phenotype cluster that the heart failure status is classified into and patient data correlated with the predetermined phenotype cluster that the heart failure status is classified into.

In an example, the heart failure statuses can be generated based on at least six sensed physiologic parameters (e.g., a first heart sound (S1), a third heart sound (S3), an intrathoracic impedance, a rapid shallow breathing index, a respiratory rate, and a heart rate). In an example, the heart failure statuses can be generated based on at least one sensed physiologic parameter (e.g., at least one of a first heart sound (S1), a third heart sound (S3), an intrathoracic impedance, a rapid shallow breathing index, a respiratory rate, or a heart rate).

The predetermined phenotype clusters can be determined by a phenotype circuit, such as the phenotype circuit 260. The phenotype circuit 260 can receive heart failure statuses and associated physiologic parameters from a group of patients (e.g., during a medical study, the phenotype circuit can receive heart failure statuses and associated physiologic parameters from patients participating in the medical study). The received heart failure statuses and physiologic parameters can be stored in a memory, such as the memory 270. The phenotype circuit 260 can organize the stored heart failure statuses and associated physiologic parameters received from the group of patients into phenotype clusters, such as to generate predetermined phenotype clusters that can be accessed by a control circuit, such as the control circuit 240.

The phenotype circuit 260 can generate phenotype clusters of heart failure statuses, such as by using an unsupervised machine learning algorithm. In an example, the phenotype clusters can be generated based on at least one of a Bayesian clustering algorithm, a hierarchal clustering algorithm, and a partitional clustering algorithm. After generating the phenotype clusters, the phenotype circuit 260 can correlate patient data with the generated phenotype clusters.

In an example, the phenotype circuit 260 can statistically correlate the patient data with the generated phenotype clusters. Patient data can include at least one demographic characteristic, a patient heart condition, a patient disease, a medical history of the patient, or a prescribed medication. In an example, the at least one demographic characteristic can include an age group of a patient, a patient ethnicity, a patient height, a patient weight, a patient geographic location, a patient marital status, or a patient income level. In an example, a patient heart condition can include congestive heart failure, arrhythmia, or high blood pressure. In an example, a patient disease can include a disease of the heart, the lungs, or any other part of the human body. In an example, the prescribed medication can include a medication prescribed for the treatment of a disease, such as heart disease.

In an example, the control circuit 240 can provide the received heart failure status to the phenotype circuit 260, such as to allow the phenotype circuit 260 to update the predetermined phenotype clusters based on the received heart failure status.

In an example, a collection of heart failure treatment systems, such as heart failure treatment system 200 can be connected to a network, such as a wireless network or the Internet. In the example, each time a heart failure status is generated by a signal analysis circuit, such as signal analysis circuit 220, a control circuit, such as control circuity 240 can provide the heart failure status to a phenotype circuit, such as phenotype circuit 260. The phenotype circuit 260 can update the predetermined phenotype clusters based on the received heart failure status, such as to provide real-time or near real-time updates of the predetermined phenotype clusters.

Figure 3:
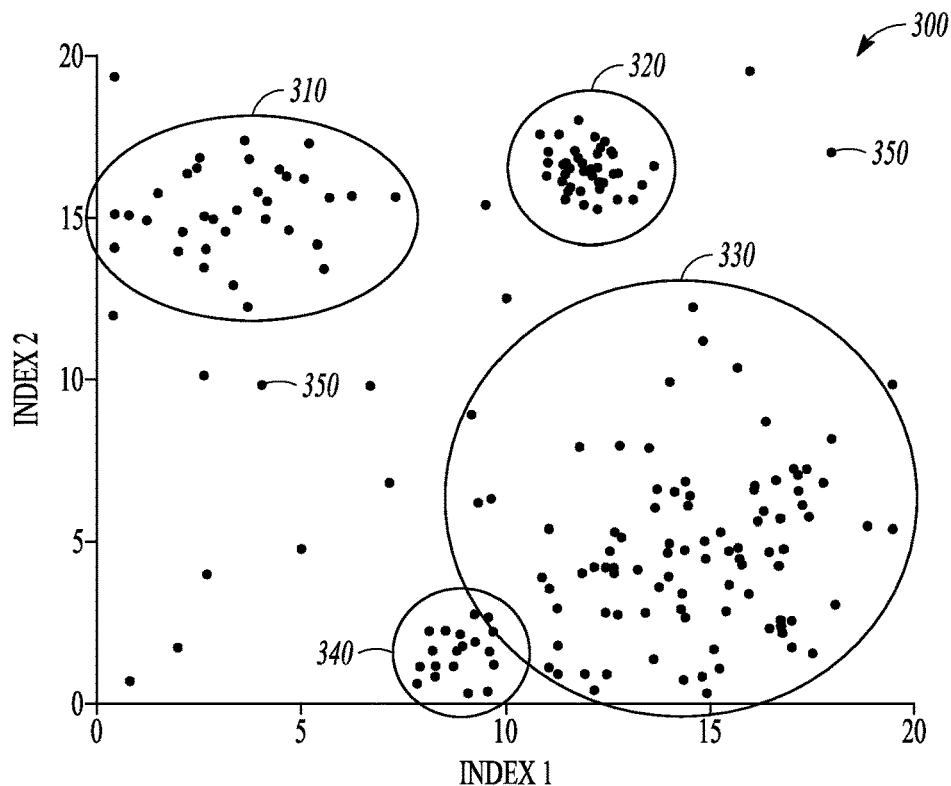
FIG. 3 illustrates an example of a diagram of phenotype clusters.

FIG. 3 illustrates an example of a diagram 300 showing predetermined phenotype clusters, such as predetermined phenotype clusters generated by the phenotype circuit 260. In the example, four predetermined phenotype clusters 310, 320, 330, and 340 can be generated from a collection of heart failure statuses 350 and associated physiologic parameters. The heart failure statuses can include a first index including numerical value in a range from 0 to 20 and a second index including a numerical value in a range from 0 to 20. The heart failure statuses 350 and associated physiologic parameters can be collected from a group of patients. The heart failure statuses 350 and associated physiologic parameters can include a first index and a second index. Each of the indices can correspond to a physiologic parameter, such as a first heart sound (S1), a third heart sound (S3), an intrathoracic impedance, a rapid shallow breathing index, a respiratory rate, or a heart rate. In an example, the first index can correspond to a first physiologic parameter (e.g., a rapid shallow breathing index), and the second index can correspond to a second physiologic parameter (e.g., a heart rate). As described above with respect to FIG. 2, each of the indices can be determined based on a statistical analysis of the stored sensed physiologic parameters corresponding to the first and second index. The numerical value of a computed index associated with a heart failure status can indicate a physiologic parameter outside of a statistically normal operating range. For example, a value of an index within 25% of a high or low end of a predetermined range can indicate a physiologic parameter significantly outside of a normal operating range. In the example illustrated in FIG. 3, an index having a value greater than 15 or less than 5 can indicate a physiologic parameter significantly outside of a normal operating range. In an example, a value of an index within 50% of a high end of a predetermined range can indicate a physiologic parameter significantly outside of a normal operating range. Each of the four predetermined phenotype clusters 310, 320, 330, and 340 can include a collection of heart failure statuses 350 as indicated by the illustrated boundaries. In the example, the first predetermined phenotype cluster 310 can include heart failure statuses having a first index within 25% of a low end of a predetermined range, and a second index within 25% of a high end of a predetermined range. Heart failure statuses 350 associated with the first predetermined phenotype cluster 310 can be indicative of a first physiologic parameter outside of a normal operating range and having an abnormally low value and a second physiologic parameter outside of a normal operating range and having an abnormally high value. The second predetermined phenotype cluster 320 can include heart failure statuses having a first index not within 25% of a high or low end of a predetermined range, and a second index within 25% of a high end of a predetermined range. Heart failure statuses 350 associated with the second predetermined phenotype cluster 320 can be indicative of a first physiologic parameter within a normal operating range and a second physiologic parameter outside of a normal operating range and having an abnormally high value. The third predetermined phenotype cluster 330 can include heart failure statuses having a first index within 50% of a high end of a predetermined range, and a second index within 50% of a low end of a predetermined range. Heart failure statuses 350 associated with the third predetermined phenotype cluster 330 can be indicative of a first physiologic parameter within a normal operating range or outside of a normal operating range and having an abnormally high value and a second physiologic parameter within a normal operating range or outside of a normal operating range and having an abnormally low value. The fourth predetermined phenotype cluster 340 can include heart failure statuses having a first index not within 25% of a high or low end of a predetermined range, and a second index within 25% of a low end of a predetermined range. Heart failure statuses 350 associated with the fourth predetermined phenotype cluster 340 can be indicative of a first physiologic parameter within a normal operating range and a second physiologic parameter outside of a normal operating range and having an abnormally low value.

While the example illustrated in FIG. 3 has been described with reference to two indices and four predetermined phenotype clusters, any number of indices and predetermined phenotype clusters are within the scope of the disclosure.

Each of the four predetermined phenotype clusters 310, 320, 330, and 340 can include heart failure statuses having similar first and second indices. The first cluster 310 can include heart failure statuses having a first index in a range of approximately 0 to 7, and a second index in a range of approximately 11 to 18. The second cluster 320 can include heart failure statuses having a first index in a range of approximately 10 to 14, and a second index in a range of approximately 14 to 19. The third cluster 330 can include heart failure statuses having a first index in a range of approximately 7 to 20, and a second index in a range of approximately 0 to 13. The fourth cluster 340 can include heart failure statuses having a first index in a range of approximately 8 to 11, and a second index in a range of approximately 0 to 4.

Some of the heart failure statuses 350 may not be assigned to a predetermined phenotype cluster. A heart failure status may not be assigned to a predetermined phenotype cluster if a distance from the unassigned heart failure status to a nearest predetermined phenotype cluster is larger than a predetermined threshold. At least two of the predetermined phenotype clusters can overlap, such as the third predetermined phenotype cluster 330 and the fourth predetermined phenotype cluster 340. When at least two of the predetermined phenotype clusters overlap, at least one heart failure status 350 can be included in more than one predetermined phenotype cluster. While four predetermined phenotype clusters have been illustrated in FIG. 3, any number of predetermined phenotype clusters can be determined by a phenotype circuit, such as the phenotype circuit 260.

Figure 4:
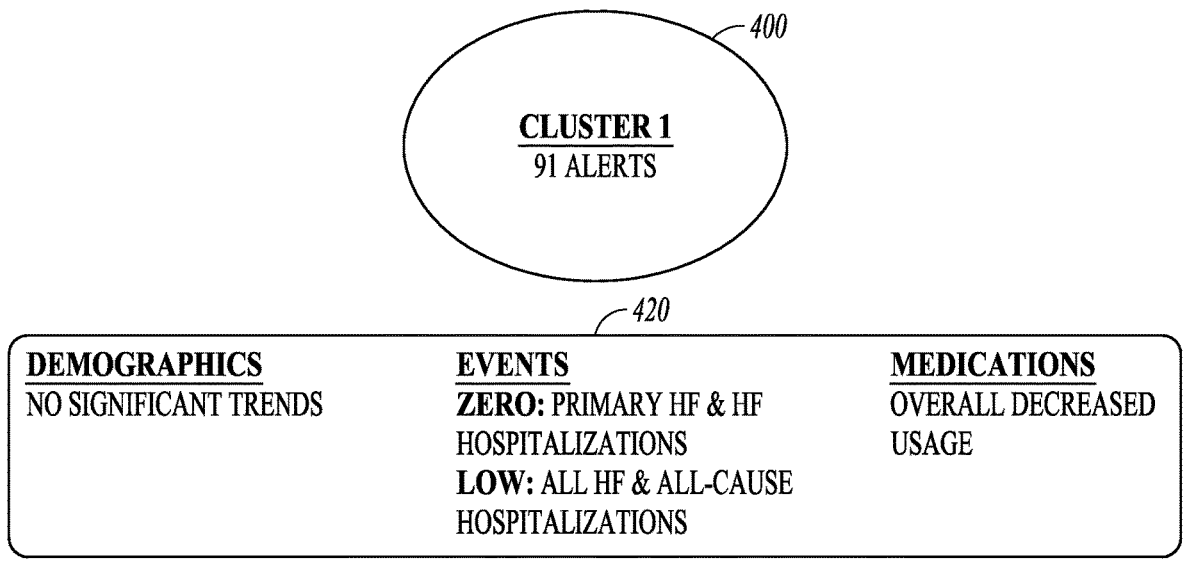
FIG. 4 illustrates an example of a phenotype cluster and correlated patient data.

FIG. 4 illustrates an example of a predetermined phenotype cluster 400 and correlated patient data 420. The predetermined phenotype cluster 400 can be generated based on stored heart failure statuses and associated physiologic parameters, such as those stored by the memory 270. The heart failure statuses in the predetermined phenotype cluster 400 can be generated based on one or more physiologic parameters, such as a first heart sound (S1), a third heart sound (S3), an implantable transthoracic total impedance (ITTI), a rapid shallow breathing index (RSBI), a respiratory rate trend (RRT), a heart rate (HR), or one or more other physiologic parameters. In certain examples, the heart failure statuses in the predetermined phenotype cluster 400 can be generated based on the at least six sensed physiologic parameters described above, or more. Further, different predetermined phenotype clusters can include heart failure statuses generated based on different changes in the same or different set of physiologic parameters. For example, a first example predetermined phenotype cluster can include relatively large changes in a first set of physiologic parameters in combination with relatively small changes in a second set of physiologic parameters, while a second example predetermined phenotype cluster can include large or small changes of different combinations of physiologic parameters. In certain examples, large can be relative to the absolute value of the sensor, a certain percentage from a high or low-end of a predetermined range, a predefined amount, a variance above or below a normal, patient-specific or population average variance, etc., whereas small can be within a percentage of a midpoint or patient-specific or population average variance, a predefined amount, etc.

The predetermined phenotype cluster 400 can include patient data 420 correlated with the stored physiologic parameters, such as patient demographics, patient hospitalization events, and patient medications. The patient hospitalization events can include primary heart failure hospitalizations as well as other non-heart failure related hospitalizations. The predetermined phenotype cluster 400 can correspond to zero primary heart failure hospitalizations and a low incidence of all-cause hospitalizations. The patient hospitalization events correlated with the predetermined phenotype cluster 400 can indicate that heart failure statuses classified into the predetermined phenotype cluster 400 may be unlikely to indicate a heart failure decompensation event, or the onset of a heart failure decompensation event. Based on the correlated patient data, including the hospitalization events, the control circuit 240 can provide a recommendation of no treatment for a patient having a heart failure status that can be classified into predetermined phenotype cluster 400.

Figure 5:
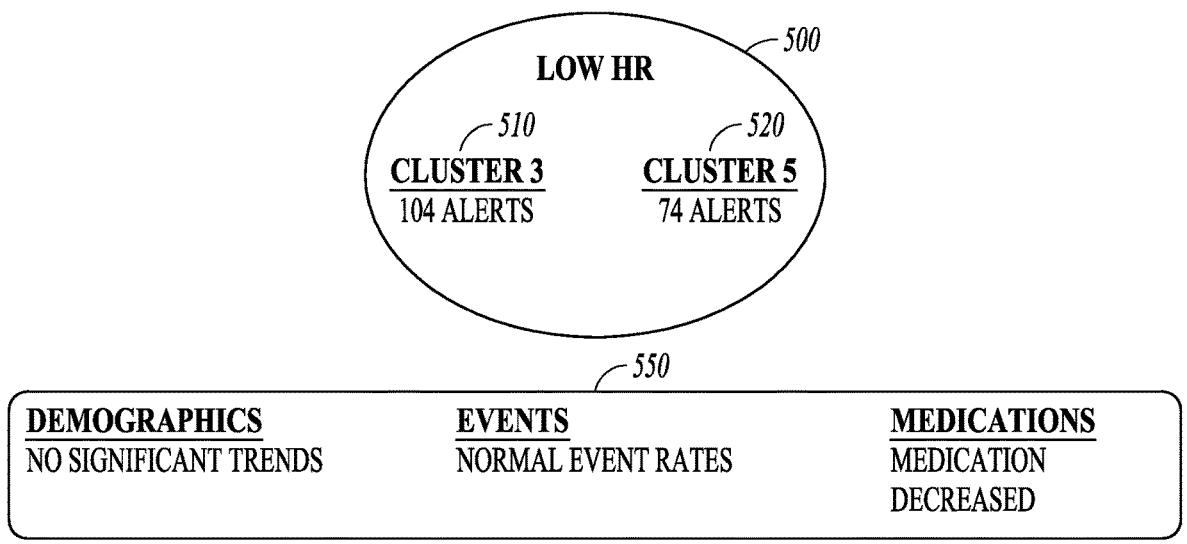
FIG. 5 illustrates an example of a phenotype cluster and correlated patient data.

FIG. 5 illustrates an example of a predetermined phenotype cluster 500 and correlated patient data. The predetermined phenotype cluster can include a first predetermined phenotype cluster 510 and a second predetermined phenotype cluster 520. Each of the first and second predetermined phenotype clusters 510 and 520 can be generated based on stored heart failure statuses and associated physiologic parameters, such as those stored by the memory 270.

In an example, the heart failure statuses in the first and second predetermined phenotype clusters 510 and 520 can be generated based on at least six sensed physiologic parameters (e.g., a first heart sound (S1), a third heart sound (S3), an implantable transthoracic total impedance ITTI, a rapid shallow breathing index RSBI, a respiratory rate RRT, and a heart rate HR). In other examples, other predetermined phenotype clusters can include different combinations or permutations of more or less physiologic parameters. In certain examples, the heart failure statuses in the predetermined phenotype clusters 510 and 520 can be generated based at least one of the six sensed physiologic parameters described above, or more. Further, different predetermined phenotype clusters can include heart failure statuses generated based on different changes in the same or different set of physiologic parameters. For example, the first predetermined phenotype cluster 510 can include relatively large changes in a first set of physiologic parameters in combination with relatively small changes in a second set of physiologic parameters, while the second predetermined phenotype cluster can include large or small changes of different combinations of physiologic parameters. The predetermined phenotype cluster 500 can include changes in at least one physiologic parameter common to both the first predetermined phenotype cluster 510 and the second predetermined phenotype cluster 520 (e.g., the predetermined phenotype cluster 500 can include large changes in a first physiologic parameter where the first predetermined phenotype cluster 510 and the second predetermined phenotype cluster 520 can include large changes in the first physiologic parameter). In certain examples, large can be relative to the absolute value of the sensor, a certain percentage from a high or low-end of a predetermined range, a predefined amount, a variance above or below a normal, patient-specific or population average variance, etc., whereas small can be within a percentage of a midpoint or patient-specific or population average variance, a predefined amount, etc.

The first and second predetermined phenotype clusters 510 and 520 can include patient data correlated with the stored heart failure statuses and associated physiologic parameters, such as patient demographics, patient hospitalization events, and patient medications. The predetermined phenotype cluster 500 can include heart failure statuses and associated physiologic parameters from the first and second predetermined phenotype clusters 510 and 520 that are generated based on a small HR. The predetermined phenotype cluster 500 can correspond to an average frequency of heart failure decompensation events. The predetermined phenotype cluster 500 may not correspond to any statistically significant patient demographics. In other examples, the predetermined phenotype cluster 500 can correspond to patient treatment of decreased medication usage, or one or more other therapies or medications. In an example, a decrease in dosage of a medication can be correlated with the predetermined phenotype cluster 500. Based on the correlated patient data, including a patient treatment, the control circuit 240 can provide a recommendation of decreased medication dosage for a patient having a future heart failure status that can be classified into predetermined phenotype cluster 500. In other examples, one or more other therapies or medications can be recommended, provided, or altered based on a heart failure status determined using one or more predetermined phenotype clusters.

Figure 6:
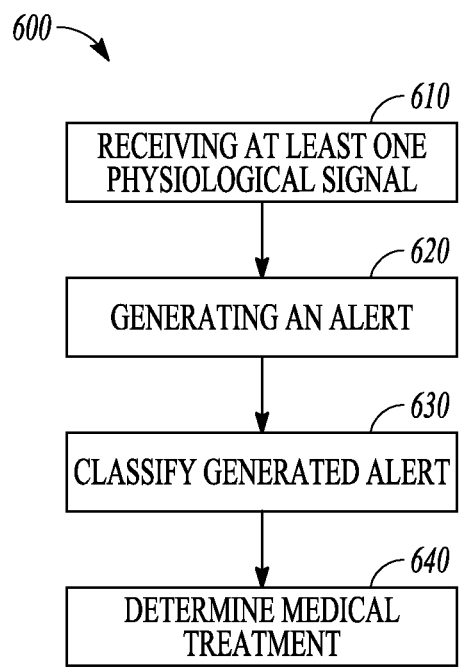
FIG. 6 illustrates a method of operating a heart failure treatment system.

FIG. 6 illustrates an example of a method of operating a heart failure treatment system, such as heart failure treatment system 200. At 610, a signal analysis circuit, such as signal analysis circuit 220 can receive physiologic information from a patient. At 620, a control circuit, such as control circuit 240 can generate a heart failure status, such as by using the received physiologic information.

At 630, the control circuit can classify the generated heart failure status into at least one of a set of predetermined phenotype clusters (e.g., a phenotype cluster that has been previously determined) based on the received physiologic information. Prior to the signal analysis circuit 220 receiving physiologic information from a patient at 610, a phenotype circuit, such as phenotype circuit 260 can determine the set of predetermined phenotype clusters based on a plurality of heart failure statuses collected from a group of patients. The phenotype circuit can correlate the set of predetermined phenotype clusters with patient data collected from the group of patients based on a statistical relationship between the set of predetermined clusters and the patient data. At 640, the control circuit can then determine a medical treatment for the patient based on the patient data from the group of patients correlated with the set of predetermined phenotype clusters. The patient data can include at least one of a patient medication, a patient heart condition, a patient disease, or a medical history of the patient. The control circuit can determine a medical treatment for the patient based on the at least one predetermined phenotype cluster that the generated heart failure status can be classified into.

Figure 7:
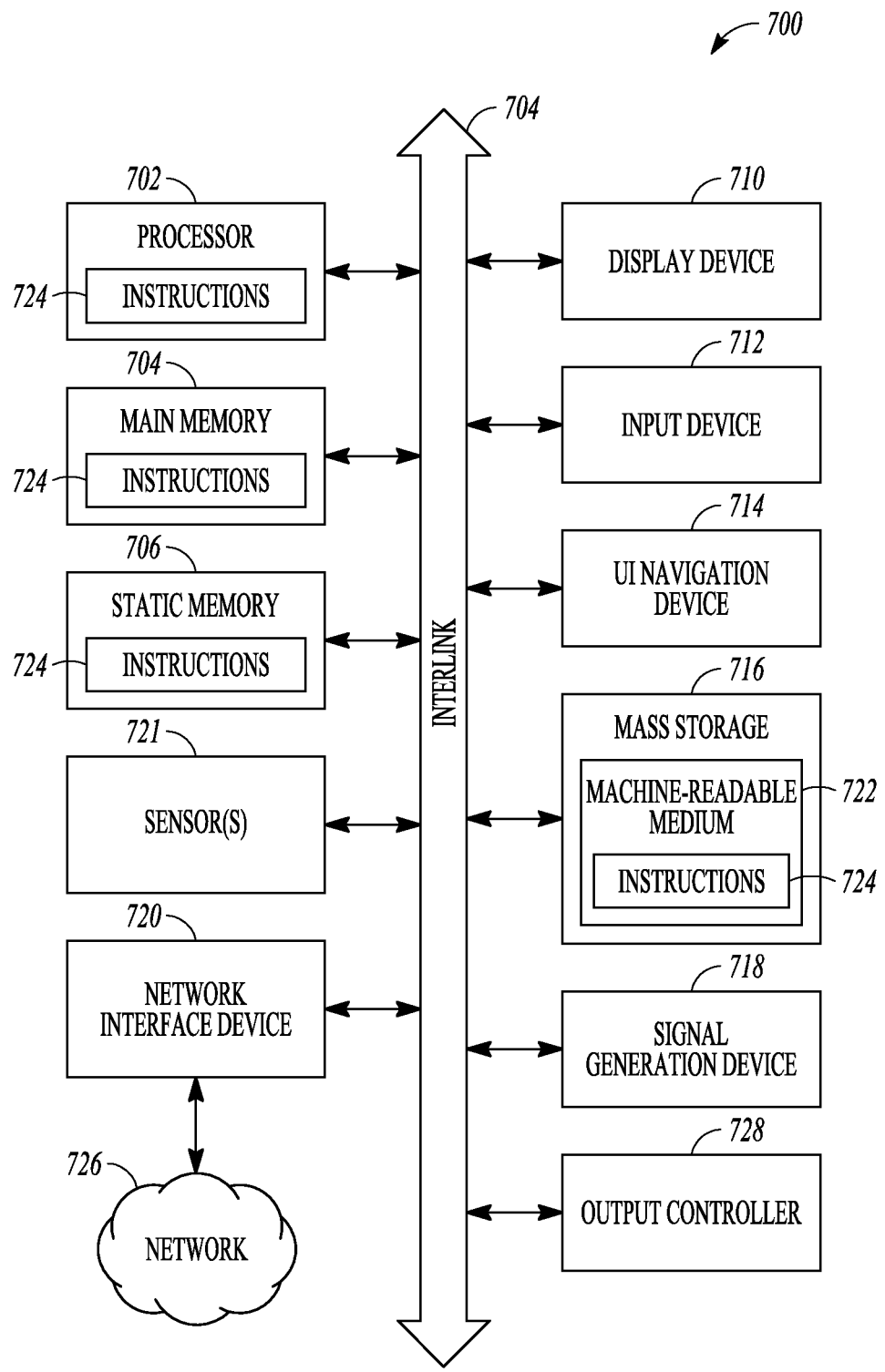
FIG. 7 illustrates a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine readable media.

While the machine readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for managing heart failure alerts through a communication link comprising:
    a sensing circuit including a heart sound sensor configured to sense a heart sound signal of a patient, a heart rate sensor configured to sense a heart rate signal of the patient, and a respiration sensor configured to sense a respiratory signal of the patient;
    a signal analysis circuit configured to receive physiologic information from the sensing circuit and to generate a heart failure status for the patient using the received physiologic information; and
    a control circuit configured to classify the generated heart failure status into at least one of a set of predetermined phenotype clusters using the received physiologic information,
    wherein the received physiologic information comprises respective first, second, third, fourth, and fifth physiologic measures of the patient, wherein the first physiologic measure comprises third heart sound (S3) information from the heart sound sensor, wherein the second physiologic measure comprises the S3 information normalized by first heart sound (S1) information from the heart sound sensor, wherein the third physiologic measure comprises rapid shallow breathing index (RSBI) information from the respiration sensor, wherein the fourth physiologic measure comprises respiratory rate information from the respiration sensor, and wherein the fifth physiologic measure comprises heart rate information from the heart rate sensor,
    wherein to generate the heart failure status for the patient, the signal analysis circuit is configured to determine a numerical index value for each of the first, second, third, fourth, and fifth physiological measures based on a statistical analysis of stored values of each respective physiological measure, to determine a composite index using the determined numerical index values, and to generate the heart failure status based on a value of the composite index,
    wherein to classify the generated heart failure status into the at least one of the set of predetermined phenotype clusters, the control circuit is configured to determine changes in the first, second, third, fourth, and fifth physiologic measures and to compare the determined changes to respective thresholds, the respective thresholds including, for each respective physiologic measure, a threshold percentage of an upper value of a predetermined patient-specific or population range or a threshold amount above a patient-specific or population average for the respective physiologic measure, and:
        to classify the generated heart failure status into a first cluster if the determined changes in the third, fourth, and fifth physiologic measures are above their respective thresholds and the determined changes in the first and second physiologic measures are below their respective thresholds;
        to classify the generated heart failure status into a second cluster if the determined change in the second physiologic measure is above its respective threshold and the determined changes in the first, third, fourth, and fifth physiologic measures are below their respective thresholds; and to classify the generated heart failure status into a third cluster if the determined changes in the second and third physiologic measures are above their respective thresholds and the determined changes in the first, fourth, and fifth physiologic measures are below their respective thresholds, wherein the control circuit is configured to automatically provide an alert for the generated heart failure status through the communication link if the generated heart failure status is classified into one of the second or third clusters and to automatically withhold the alert for the generated heart failure status, omitting the alert through the communication link, if the generated heart failure status is classified into the first cluster.

2. The system of claim 1, wherein the control circuit is configured to determine a medical treatment for the patient based on the at least one predetermined phenotype cluster and the generated heart failure status, including to determine a reduced medication dosage indication for the patient if the generated heart failure status is classified into one of the second or third clusters.

3. A method for managing heart failure alerts through a communication link comprising:

sensing a heart sound signal of a patient using a heart sound sensor of a sensing circuit, a heart rate signal of the patient using a heart rate sensor of the sensing circuit, and a respiratory signal of the patient using a respiration sensor of the sensing circuit;

receiving, using a signal analysis circuit, physiologic information from a patient the sensing circuit;

generating, using the signal analysis circuit, a heart failure status for the patient using the received physiologic information; and classifying, using a control circuit, the generated heart failure status into at least one of a set of predetermined phenotype clusters using the received physiologic information;

wherein the received physiologic information comprises respective first, second, third, fourth, and fifth physiologic measures of the patient, wherein the first physiologic measure comprises third heart sound (S3) information from the heart sound sensor, wherein the second physiologic measure comprises the S3 information normalized by first heart sound (S1) information from the heart sound sensor, wherein the third physiologic measure comprises rapid shallow breathing index (RSBI) information from the respiration sensor, wherein the fourth physiologic measure comprises respiratory rate information from the respiration sensor, and wherein the fifth physiologic measure comprises heart rate information from the heart rate sensor, wherein generating the heart failure status for the patient includes determining a numerical index value for each of the first, second, third, fourth, and fifth physiological measures based on a statistical analysis of stored values of each respective physiological measure, determining a composite index using the determined numerical index values, and generating the heart failure status based on a value of the composite index, wherein classifying the generated heart failure status into the at least one of the set of predetermined phenotype clusters comprises determining relatively large or small changes in the first, second, third, fourth, and fifth physiologic measures and comparing the determined changes to respective thresholds, the respective thresholds including, for each respective physiologic measure, a threshold percentage of an upper value of a predetermined patient-specific or population range or a threshold amount above a patient-specific or population average for the respective physiologic measure, and:

classifying the generated heart failure status into a first cluster if the determined changes in the third, fourth, and fifth physiologic measures are above their respective thresholds and the determined changes in the first and second physiologic measures are below their respective thresholds;

classifying the generated heart failure status into a second cluster if the determined change in the second physiologic measure are above their respective thresholds and the determined changes in the first, third, fourth, and fifth physiologic measures are below their respective thresholds; and classifying the generated heart failure status into a third cluster if the determined changes in the second and third physiologic measures are above their respective thresholds and the determined changes in the first, fourth, and fifth physiologic measures are below their respective thresholds, wherein the method includes automatically providing an alert for the generated heart failure status through the communication link if the generated heart failure status is classified into one of the second or third clusters and automatically withholding an alert for the generated heart failure status, omitting the alert through the communication link, if the generated heart failure status is classified into the first cluster.

4. The method of claim 3, further comprising determining a medical treatment for the patient based on the at least one predetermined phenotype cluster and the generated heart failure status, wherein determining the medical treatment for the patient comprises determining a reduced medication dosage indication for the patient if the generated heart failure status is classified into one of the second or third clusters.

5. A system for managing heart failure alerts through a communication 25. link comprising:

a sensing circuit including a heart sound sensor configured to sense a heart sound signal of a patient, a heart rate sensor configured to sense a heart rate signal of the patient, and a respiration sensor configured to sense a respiratory signal of the patient;

a signal analysis circuit configured to receive physiologic information from the sensing circuit and to generate a heart failure status for the patient using the received physiologic information; and a control circuit configured to classify the generated heart failure status into at least one of a set of predetermined phenotype clusters using the received physiologic information, wherein the received physiologic information comprises first and second physiologic measures of the patient, wherein the first physiologic measure comprises third heart sound (S3) information from the heart sound sensor normalized by first heart sound (S1) information from the heart sound sensor, and wherein the second physiologic measure comprises heart rate information from the heart rate sensor, wherein to generate the heart failure status for the patient, the signal analysis circuit is configured to determine a numerical index value for each of the first and second physiological measures based on a statistical analysis of stored values of each respective physiological measure, to determine a composite index using the determined numerical index values, and to generate the heart failure status based on a value of the composite index,
wherein to classify the generated heart failure status into at least one of a set of predetermined phenotype clusters, the control circuit is configured to determine changes in the first and second physiologic measures and to compare the determined changes to respective thresholds, the respective thresholds including, for each respective physiologic measure, a threshold percentage of an upper value of a predetermined patient-specific or population range or a threshold amount above a patient-specific or population average for the respective physiologic measure, and:
to classify the generated heart failure status into a first cluster if the determined change in the second physiologic measure is above its respective threshold and the determined change in the first physiologic measure is below its respective threshold; and
to classify the generated heart failure status into a second cluster if the determined change in the first physiologic measure is above its respective threshold and the determined change in the second physiologic measure is below its respective threshold,
wherein the control circuit is configured to automatically provide an alert for the generated heart failure status if the generated heart failure status is classified into the second cluster and to automatically withhold the alert for the generated heart failure status if the generated heart failure status is classified into the first cluster.

6. The system of claim 5, wherein the control circuit is configured to determine a medical treatment for the patient based on the at least one predetermined phenotype cluster and the generated heart failure status, including to determine a reduced medication dosage indication for the patient if the heart failure status is classified into the second cluster to alleviate future alerts.

7. The system of claim 1, wherein the threshold percentage of the upper value of the predetermined patient-specific or population range or the threshold amount above the patient-specific or population average of the respective physiological measure comprises within 50% of the upper value of a predetermined range for the respective physiological measure, and
wherein the threshold amount above the patient-specific or population average of the respective physiological measure comprises within 50% of a lowest value of the respective physiological measure.

8. The system of claim 1, wherein the threshold percentage of the upper value of the predetermined patient-specific or population range or the threshold amount above the patient-specific or population average of the respective physiological measure comprises within 25% of the upper value of a predetermined range for the respective physiological measure, and
wherein the threshold amount above the patient-specific or population average of the respective physiological measure comprises within 25% of a lowest value of the respective physiological measure.

9. The method of claim 3, wherein the threshold percentage of the upper value of the predetermined patient-specific or population range or the threshold amount above the patient-specific or population average of the respective physiological measure comprises within 50% of the upper value of a predetermined range for the respective physiological measure, and
wherein the threshold amount above the patient-specific or population average of the respective physiological measure comprises within 50% of a lowest value of the respective physiological measure.

10. The method of claim 3, wherein the threshold percentage of the upper value of the predetermined patient-specific or population range or the threshold amount above the patient-specific or population average of the respective physiological measure comprises within 25% of the upper value of a predetermined range for the respective physiological measure, and
wherein the threshold amount above the patient-specific or population average of the respective physiological measure comprises within 25% of a lowest value of the respective physiological measure.

11. The system of claim 5, wherein the threshold percentage of the upper value of the predetermined patient-specific or population range or the threshold amount above the patient-specific or population average of the respective physiological measure comprises within 50% of the upper value of a predetermined range for the respective physiological measure.

12. The system of claim 5, wherein the threshold percentage of the upper value of the predetermined patient-specific or population range or the threshold amount above the patient-specific or population average of the respective physiological measure comprises within 25% of the upper value of a predetermined range for the respective physiological measure.

13. The system of claim 1, wherein the signal analysis circuit is configured to:
create at least one index for each of the heart sound signal, the heart rate signal, and the respiration signal of the patient;
form a composite index using the created indices, each of the created indices corresponding to a physiological parameter; and
generate the heart failure status for the patient using the composite index, wherein the control circuit is configured to classify the generated heart failure status into at least one of the set of predetermined phenotype clusters using the created indices.

14. The system of claim 1, wherein to automatically withhold the alert comprises to determine that no treatment should be provided.

15. The system of claim 1, wherein the alert comprises a recommendation for treatment.

16. The system of claim 1, comprising a phenotype circuit configured to:
generate the set of predetermined phenotype clusters using an unsupervised machine learning algorithm including at least one of a Bayesian clustering algorithm, a hierarchical clustering algorithm, or a partitional clustering algorithm on collected physiological information from a group of patients;
correlate the received physiological information from the sensing circuit to the generated phenotype clusters; and
update the predetermined phenotype clusters based on the generated heart failure status.

17. The method of claim 3, comprising:
creating, using the signal analysis circuit, at least one index for each of the heart sound signal, the heart rate signal, and the respiration signal of the patient; and
forming, using the signal analysis circuit, a composite index using the created indices, each of the created indices corresponding to a physiological parameter; and wherein generating the heart failure status for the patient comprises using the composite index, wherein classifying the generated heart failure status into at least one of the set of predetermined phenotype clusters includes using the created indices.

18. The method of claim 3, wherein automatically withholding the alert comprises determining that no treatment should be provided.

19. The method of claim 3, wherein the alert comprises a recommendation for treatment.

20. The method of claim 3, comprising:
generating, using a phenotype circuit, the set of predetermined phenotype clusters using an unsupervised machine learning algorithm including at least one of a Bayesian clustering algorithm, a hierarchical clustering algorithm, or a partitional clustering algorithm on collected physiological information from a group of patients;
correlating, using the phenotype circuit, the received physiological information from the sensing circuit to the generated phenotype clusters; and
updating, using the phenotype circuit, the predetermined phenotype clusters based on the generated heart failure status.

* * * * *